United States Patent [19]

Gergely et al.

[11] Patent Number: 5,158,779
[45] Date of Patent: Oct. 27, 1992

[54] PARTICLES OF HYDROPHOBIC OR SPARINGLY SOLUBLE SUBSTANCE

[76] Inventors: Gerhard Gergely; Thomas Gergely; Irmgard Gergely, Gartengasse 8, all of A-1050 Vienna, Austria

[21] Appl. No.: 266,350

[22] Filed: Nov. 2, 1988

Related U.S. Application Data

[63] Continuation of Ser. No. 897,533, Aug. 1, 1986, abandoned.

[30] Foreign Application Priority Data

Dec. 14, 1984 [CH] Switzerland ............... 5941/84

[51] Int. Cl.$^5$ ............... A61K 9/14; A61K 31/43
[52] U.S. Cl. ............... 424/490; 424/491; 424/493; 424/496; 424/497
[58] Field of Search ............... 424/502, 466, 78, 493, 424/482, 479, 489, 491, 490, 496, 497; 428/357

[56] References Cited

U.S. PATENT DOCUMENTS

| | | | |
|---|---|---|---|
| 3,887,700 | 6/1975 | Bonsey et al. | 424/44 |
| 3,920,442 | 11/1975 | Albert et al. | 424/44 |
| 4,344,934 | 8/1982 | Martin et al. | 424/80 |

FOREIGN PATENT DOCUMENTS

| | | |
|---|---|---|
| 368880 | 11/1982 | Austria. |
| 3149517 | 7/1982 | Fed. Rep. of Germany. |
| 2218085 | 9/1974 | France. |
| 970462 | 9/1964 | United Kingdom. |

OTHER PUBLICATIONS

O. A. Neumuller, "Romps Chemie-Lexikon," 7th Ed., vol. 5, p. 3083 (1975).

Primary Examiner—Thurman K. Page
Assistant Examiner—Peter F. Kulkosky
Attorney, Agent, or Firm—Marmorek, Guttman & Rubenstein

[57] ABSTRACT

The surface of micronized and hydrophilized powder particles of a hydrophobic or sparingly soluble substance is covered with a cohesive layer of not more than 0.1 part by weight of surfactant in not more than 10 parts by weight of a binder (based on 100 parts by weight of the substance). A sparingly soluble or insoluble antibiotic is converted to instant granules or instant tablets, while a hydrophobic, moderately soluble to readily soluble pharmaceutical substance, such as, for example, acetylsalicylic acid or paracetamol, is converted to effervescent granules or effervescent tablets. The particles are preferably applied to carbohydrate crystals by means of a binder. The preparation is carried out by a method in which a solution which contains at least one surfactant in an amount of 0.01 to 0.1% by weight, based on the weight of the particles to be hydrophilized, and a binder in an amount corresponding to 5 to 10 times the weight of the surfactant used is sucked through a bed of the particles under a pressure of less than 800, preferably less than 100, mbar.

19 Claims, No Drawings

PARTICLES OF HYDROPHOBIC OR SPARINGLY SOLUBLE SUBSTANCE

This is a continuation of application Ser. No. 897,533, filed Aug. 1, 1986 now abandoned.

The present invention relates to micronized and hydrophilized particles of a hydrophobic or sparingly soluble substance to which a surfactant has been added, and a process for hydrophilizing these particles, in particular of pharmaceutical active substances, for example by wetting the particle surface with a solution of a surfactant and evaporating the solvent from the particle surface.

Although care has been taken to date to achieve very thorough and homogeneous mixing, or distribution of the surfactant on the active substance, no attention has been paid to the fact that the distribution can be considered as being good only on the macro scale. However, dissolution or dispersing of such particles in water is dependent on the surface of each individual particle, which is frequently only 1 to 5 microns in size, i.e. on the micro scale. With the mixing methods proposed to date, for example according to AP-A 368,880 or U.S. Pat. No. 4,344,934, it was therefore necessary to use relatively large amounts of surfactant (for example 0.15 to 0.5 part per 100 parts of active substance) and/or very large amounts of solvent. When the particles are introduced into water, particularly when they are used in effervescent tablets, the first measure causes undesirably vigorous foaming, apart from the fact that large amounts of surfactants are undesirable for health reasons. The second measure requires an expensive spray-drying process in which a surfactant is added, which in turn is not homogeneously distributed.

In all these cases, surfactant molecules are in fact agglomerated on isolated areas of the surface of the particles of the substance, whereas other surface areas remain uncovered because the air adhering to the surface, which is frequently large, prevents contact with the surfactant molecules. On contact with water, the excess surfactant concentrated in isolated areas of the particle surface first goes into solution and causes undesirable foaming during the further procedure; the particles having the predominantly hydrophobic and/or sparingly soluble surface, to which surfactant adheres only in a few areas, are only poorly dispersed because the surfactant, although present in excess relative to the substance, is much too dilute in the aqueous solution and hence can no longer be effective.

It is therefore the object of the invention to hydrophilize hydrophobic or sparingly soluble particles, this being achieved by the measures which are stated in claims 1 to 5 and are particularly advantageously effected by the process steps described in claims 6 to 11.

Although it is possible in principle to obtain a virtually uniform coating on the particles of the substance if a surfactant is applied in very large amounts of solvent to the particle bed, and the latter is dried with constant stirring, this requires a great deal of time and energy, and the recovery of large amounts of solvent is not pleasant.

Despite acceptable wettability or adequate solubility in water, a number of organic substances exhibit a certain hydrophobic behavior toward water. Active substances, such as certain antibiotics, which are insoluble in water but are to be suspended, therefore require a certain amount of time before they adhesively bind certain amounts of water to the crystal surface, so that, after a certain treatment time, they float freely in water. Even in the case of some water-soluble substances, such as, for example, the relatively readily water-soluble acetylsalicylic acid, a certain amount of time is nevertheless required in order to bring them into solution, especially in cold water. Paracetamol and other active substances exhibit similar behavior.

In order to eliminate or improve these phenomena, attempts have constantly been made to improve the solubility or dispersability of such active substances by means of surface-active or wash-active substances. Since relatively large amounts of such substances were used, unpleasant foaming and unattractive dissolution patterns occurred, especially when the active substances were used in effervescent tablets. Attempts have already been made to incorporate wash-active substances during recrystallization or during the final purification of active substances. However, these efforts were without success. In fact, surfactants initially remain in the mother liquor during crystallization of the active substances and are salted out in coarse form by the remaining impurities, without adhering uniformly to the surface of the active substance in a thin layer. Film formation cannot be achieved simultaneously with recrystallization, purification or washing of the crystal.

It is possible to obtain active substances as described in claims 1 to 5, particularly—but not solely—by applying a vacuum. This procedure includes the application of various solvents, mixtures and various concentrations, preferably for each substance, so that optimum film formation takes place on the surface of the crystal.

The present invention proposes a simple process for achieving such effects, wherein only traces of wash-active substances have to be used in order to achieve adequate effects. Traces of substances are particularly thoroughly distributed over a finely divided carrier in vacuo by removing the air layers surrounding the crystals, application being effected under special conditions.

If in fact a dissolved substance, such as, for example, dioctyl sulfosuccinate in methylene chloride, is applied onto, for example, erythromycin succinate having a size of 5–10 microns, and the methylene chloride is vaporized, unless suitable measured are taken concentration of the very dilute solution will take place in a known manner, so that, on drying, islands are formed which finally result in a small portion of the crystals receiving a relatively large amount of surfactant substance while the rest remains uncovered.

The process according to the invention makes it possible to apply the surfactants, in ppm amounts, uniformly onto substances, and to alter the solution or dispersion behavior of substances in such a way, without however critically changing their composition or physiological behavior.

In an embodiment of the process according to the invention, the total amount of solution can first be sucked through the bed of substance, after which a stream of air can be passed through the bed until the solvent has evaporated. The solvent can also be evaporated off under reduced pressure, in the absence of a stream of air.

In a variant of the process according to the invention, the solution is added dropwise to a stream of air passed through the bed of the substance to be hydrophilized, at the inlet into a vacuum kettle; during passage of the mixture consisting of solution and air through the bed, the mixture is distributed and the solvent continuously evaporated as a result of the turbulence produced in vacuo and with simultaneous stirring. When the solution has been consumed, further air may be passed through the bed in order to evaporate off from the hydrophilized substance any amounts of solvent still adhering.

If required by these process conditions, the air used as an evaporating agent or as a carrier gas for the solution can be preheated. In the case of oxygen-sensitive substances, a gas which is inert to these substances, such as nitrogen, can be employed instead of air.

When air is used as a carrier gas for the solution, the air, which contains the solution in an amount of 5–10% by weight, based on the substance to be hydrophilized, is preferably passed through the bed in an amount of 100–500 l/min per 100 kg of the substance to be hydrophilized.

A liquid having a vapor pressure of less than 2 mbar at 25° C., such as, in particular, a polyhydric alcohol, an aldehyde or a ketone, is preferably employed as the antifoam.

The small amount of adhesive, such as, for example, polyvinylpyrrolidone, carboxymethylcellulose and the like, which is applied, together with the surfactant, onto the substance to be hydrophilized serves to fix the surfactant on the surface of the substance.

By using the extremely small amounts of surfactant, foaming and the resulting bubble formation, particularly where the hydrophilized substances are used in effervescent tablets, are very substantially reduced. In order reliably and completely to suppress the bubble formation mentioned, it has proven advantageous if a liquid having a low vapor pressure of less than 2 mbar at 25° C. is applied, simultaneously with the surfactant and the adhesive, to the substance to be hydrophilized. Examples of compounds which are particularly suitable for this purpose are relatively high molecular weight alcohols, aldehydes and ketones, for example benzyl alcohol.

Thus, the ease with which water-soluble substances, such as, for example, carbocisteine, amoxycillin, erythromycin succinate, etc., can be suspended is improved by means of the hydrophilization process according to the invention. Furthermore, the rate of dissolution of sparingly soluble substances in water can be increased if such substances are treated with very small amounts of surfactant and adhesive, as is the case, for example, for paracetamol, acetylsalicylic acid, ampicillin, etc. After treatment, these substances exhibit immediate immersion in water, i.e. they do not remain floating on the surface but immediately submerge, go into suspension or dissolve with gentle stirring.

Using the process according to the invention, it is possible in principle to hydrophilize any substance which it is intended to dissolve or suspend in water. However, the process according to the invention is particularly suitable for pharmaceutical active substances which are to be suspended or dissolved in water. These hdyrophilized active substances can, for example, also be contained in powder mixtures for the preparation of instant beverages or in effervescent tablets.

In the case of the instant products, the hydrophilized substances, where these additionally contain a binder, such as, for example, polyvinylpyrrolidone, can be applied to sugar crystals simply by mixing. Because of this adhesive power, coatings of such substances on carbohydrate crystals can relatively easily be prepared, for example by means of a simple mixing process. The hydrophilized substances are substances pretreated in this manner, which, when mixed in the dry state with sugar crystals, exhibit adhesive power and go into suspension from the sugar crystal.

This applies not only to the antibiotics already mentioned but, for example, also to paracetamol. Untreated paracetamol in an effervescent tablet has a very pronounced tendency to foam and the rate of dissolution is substantially slowed down, with the result that particles rise to the surface, do not dissolve, form a film on the surface of the beverage and tend to produce unattractive foam, whereas hydrophilized paracetamol dissolves simultaneously with the effervescent mixture to give a clear solution. The same applies to acetylsalicylic acid whose surface has not been treated and which is processed in effervescent mixtures, so that when an attempt is made to dissolve the effervescent tablet the crystals float to the surface and rest against the edge of the glass, whereas in the case of the treated active substance the crystals sink in the water and then dissolve in the solution to give a clear solution.

Anionic, cationic or nonionic surfactants can be used as surfactants in the process according to the invention. Examples of suitable surfactants are dioctyl sulfosuccinate, polysorbate and the like.

The invention is illustrated in more detail by the examples which follow. In the examples, a rotatable vacuum kettle equipped with a stirrer, a heating jacket and a discharge sieve was used. A vacuum kettle which is particularly suitable for the purposes according to the invention is described in Austrian Patents 375,279 and 376,147. In the examples, all parts and percentages are based on weight, unless stated otherwise.

EXAMPLE 1

100 parts of micronized erythromycin succinate having a crystal size of 5–10 microns are treated with 0.1 part of dioctyl sulfosuccinate and 3 parts of polyvinylpyrrolidone, dissolved in 8 parts of alcohol.

The erythromycin succinate is heated to 40° C., at a jacket temperature of 50° C. The pressure is then reduced to about 50 mbar and the solution is slowly sucked in with three-dimensional stirring (swinging stirring) at maximum speed. The suction process should last about 3–5 minutes.

The pressure is then reduced to a final value of 20 mbar while continuing the thorough stirring. The erythromycin succinate is then discharged, for example via a rotating sieve.

EXAMPLE 2

100 parts of micronized ampicillin anhydride are treated with 0.01 part of dioctyl sulfosuccinate and 1 part of polyvinylpyrrolidone, dissolved in 4 parts of alcohol. Further treatment is carried out as described under Example 1.

EXAMPLE 3

100 parts of amoxycillin trihydrate are treated with 0.1 part of "Tween" (polysorbate 80), 2 parts of polyvinylpyrrolidone and 2 parts of ethylcellulose having a short chain length, dissolved in 4 parts of alcohol and 2 parts of methylene chloride.

Since amoxycillin trihydrate tends to exhibit losses on drying, the treatment is carried out continuously in a stream of air. The jacket temperature is only 40° C., and a stream of 100 parts of air per minute is allowed to flow through under reduced pressure of 800 mbar with thorough three-dimensional stirring (i.e. 100 l of air/min for 100 kg of material).

The above-mentioned solution is introduced into the air stream directly upstream of the inlet nozzle, by means of a stock vessel, so that the entire solution is distributed in the material via the air stream in about 5 minutes. About 70-80% of the solvent evaporates during this time. Hence, the stream of air must be allowed to flow through for about 10-15 minutes longer in order to evaporate the remainder of the solvent. Residues of adsorbed solvent are removed by completely evacuating the material down to 10-20 mbar, in the absence of a stream of air.

EXAMPLE 4

100 parts of carbocisteine are treated with 0.1 part of dioctyl sulfosuccinate and 2 parts of polyvinylpyrrolidone in a solution of 5 parts of methylene chloride. Since methylene chloride evaporates particularly rapidly, the treatment should be carried out in a stream of air.

Carbocisteine is therefore preheated to 40° C. at a jacket temperature of 50° C. The kettle is evacuated, and a stream of 100 parts of air per minute is sucked through the material under 800 mbar and with vigorous three-dimensional stirring. The solution is introduced into this stream of air at a rate of 1 part of solution per minute. It condenses on the carbocisteine and evaporates from it, these processes taking place continuously.

In this case, the air can be preheated to 40° C. so that, because of the heat of vaporization of methylene chloride, no temperature loss results. The entire solution is introduced in the course of about 5 minutes; vigorous stirring is carried out for a further 3 minutes with further passage of air, after which evacuation down to 10 mbar is effected in order to eliminate the residual amounts of methylene chloride.

EXAMPLE 5

100 parts of paracetamol (particle size 100 microns) are treated with 0.01 part of dioctyl sulfosuccinate, 1 part of polyvinylpyrrolidone and 0.5 part of benzyl alcohol, which are dissolved in 12 parts of methylene chloride.

The paracetamol is preheated to 50° C. (at a jacket temperature of 60° C.) and evacuated down to 20 mbar, and the solution is introduced by causing it to flow into the material under about 50 mbar (with the valve to the vacuum pump closed). Because of the vaporizing solvent, a generally constant pressure of about 200 mbar results, and three-dimensional stirring is carried out for about 5 minutes to effect complete distribution of the solvent.

Evacuation down to 200 mbar is then effected with vigorous stirring, some of the benzyl alcohol evaporating, but about 70% of the amount of benzyl alcohol remaining in the coating on the paracetamol.

Finally, the kettle is once again evacuated down to 10-20 mbar. The material discharged through the sieve must not be in an agglomerated state.

EXAMPLE 6

100 parts of acetylsalicylic acid are treated with a solution of 0.2 part of polyvinylpyrrolidone and 0.03 part of dioctyl sulfosuccinate in 6 parts of ethyl alcohol.

It is possible to use either the process described under Example 1 or that described under Example 3. In the case of larger amounts, however, it is advisable to use the batchwise procedure, since these coatings are more difficult to produce on acetylsalicylic acid.

In this process, 100 parts of acetylsalicylic acid are preheated to 45° C. at a jacket temperature of 55° C. and subjected to vigorous three-dimensional stirring. The kettle is evacuated down to 20 mbar, and the solution is then introduced at a rate such that the entire solution takes about 5 minutes to flow in. Mixing is continued for a further 5 minutes as before, after which evaporation is effected by opening the valve to the vacuum pump. Here, it is advantageous to allow 100 parts of air per minute to flow through under a constant vacuum of 600-800 mbar, when evaporating the solvent. This flow of air results in the solvent being removed uniformly; however, the turbulence of the air jet helps to maintain the film of dioctyl sulfosuccinate and polyvinylpyrrolidone, which, particularly in the case of acetylsalicylic acid, is difficult to achieve and requires special precautions.

After the air has flowed through for about 10 minutes under a constant vacuum, the inlet valve for the air is closed, and the kettle is evacuated down to a final value of 10 mbar.

EXAMPLE 7

It is possible, in the preparation of effervescent tablets, to adopt a procedure in which an effervescent tablet mixture is mixed with the acetylsalicylic acid treated on the surface as described in the above-mentioned Example, and the mixture is pressed. On dissolution, such tablets do not exhibit the usual unpleasant border of undissolved crystals on the glass, but instead exhibit completely uniform dissolution behavior. The acetylsalicylic acid dissolves in the water simultaneously with the effervescent mixture to give a clear solution.

EXAMPLE 8

In other cases, the process according to the invention can be used to carry out granulation by producing a coating on a carrier, simultaneously with the treatment of the surface of the active substance.

10 parts of carbocisteine are added to 100 parts of sugar: the mixture is heated to 50° C. in a vacuum kettle. The sugar preferably has a crystal size of 0.2-0.3 mm, while the carbocisteine should have a crystal size of 5-10 microns.

The kettle is then evacuated down to 20 mbar, and a solution of 0.1 part of dioctyl sulfosuccinate and 2 parts of polyvinylpyrrolidone in 6 parts of alcohol is introduced uniformly onto the entire mass in the course of 2 minutes.

After three-dimensional dispersing has been carried out for a further 3 minutes, the vacuum valve is opened and the alcohol evaporated.

Further adhesion of the carbocisteine to the sugar can be effected by introducing a further 2% of an aqueous sugar solution, consisting of 1 part of water and 1 part of sugar, into the vacuum kettle under the same conditions. The kettle is evacuated down to 50 mbar, and this concentrated sugar solution is allowed to flow in, once again during a period of 2-3 minutes.

Three-dimensional stirring is carried out for a further 3 minutes, after which the kettle is completely evacuated until a final vacuum of 20 mbar is reached.

This material can be provided with colorants, flavor adjusters and sweeteners, and gives granules which, after being introduced into water, keep carbocisteine floating freely in suspension.

EXAMPLE 9

1000 mg of hydrophobic micronized active substance, for example one of the antibiotics mentioned in the preceding Examples, are ground vigorously in a dish with 0.1 mg of dioctyl sulfosuccinate and 30 mg of polyvinylpyrrolidone in 80 mg of alcohol. The powder is then dried, and 100 mg of the dry powder are introduced into 100 ml of water and stirred for a short time. After 3 minutes, particles exhibiting poor wetting and agglomerated lumps, some of them at the surface of the water and some at the bottom, remain.

100 mg of the same active substance are introduced into 100 ml of water to which only 0.01 mg of dioctyl sulfosuccinate have been added. The major part of the active substance is not wet and is poorly dispersed; the difference with respect to pure water is negligible.

100 mg of the active substance treated according to Example 1 are introduced onto the surface of 100 ml of water. They sink to the bottom separately as individual particles in the course of 30 seconds, and give a suspension which is pleasant to drink, after stirring has been carried out for a short time.

We claim:

1. A hydrophilized composition, comprising
   individual micronized particles of a hydrophobic or sparingly soluble pharmaceutically active substance,
   each of said individual particles being coated with a cohesive layer consisting essentially of surfactant and binder and containing substantially no active agent, said cohesive layer being bound to the surface of said particles, said cohesive layer comprising about 0.01 to about 0.1 parts by weight of surfactant, and about 0.2 to about 10 parts by weight of binder based on 100 parts by weight of said substance.

2. The composition of claim 1 comprising about 0.05 parts by weight of surfactant and about 6 parts by weight of binder.

3. The composition of claim 1 wherein said substance comprises a pharmaceutically active substance.

4. The composition of claim 1 wherein said substance is a pharmaceutically active substance selected from the group comprising erythromycin succinate, amoxycillin, penicillin, carbocisteine, acetylsalicylic acid, and paracetamol.

5. The composition of claim 1 in the form of instant granules or tablets.

6. The composition of claim 1 in the form of effervescent granules or tablets.

7. The composition of claim 1 further comprising carbohydrate crystals, said particles being applied to said carbohydrate crystals.

8. The composition of claim 1 further comprising an antifoaming agent.

9. A method for hydrophilizing micronized particles of a hydrophobic or sparingly soluble substance, comprising
   dissolving at least one surfactant in an amount of about 0.1 to 0.1% percent by weight, based on the weight of particles to by hydrophilized, and a binder in an amount corresponding to about 5 to 10 times the weight of said surfactant, in a solvent to form a solution,
   applying said solution to the surface of said particles by sucking said solution through a bed of said particles under reduced pressure, and
   evaporating said solvent to produce a composition of micronized particles with a cohesive layer consisting essentially of surfactant and binder and containing substantially no active agent, said cohesive layer being bound thereto.

10. The method of claim 9 wherein said reduced pressure is less than 800 mbar.

11. The method of claim 9 wherein said reduced pressure is less than 100 mbar.

12. The method of claim 9 further comprising passing a gas stream through said bed of particles after said solution has been sucked through said bed of particles.

13. The method of claim 12 wherein said gas stream comprises a stream of air.

14. The method of claim 9 wherein said solution is applied to said particles by a gas stream passing through said bed of particles.

15. The method of claim 14 wherein said gas stream comprises a stream of air.

16. The method of claim 14 wherein said gas stream contains said solution in an amount of 5 to 10% by weight, based on the weight of particles, and said gas stream is passed through said bed of particles at a rate of 100 to 500 l/min per 100 kg of said particles.

17. The process of claim 9 further comprising applying an antifoaming agent in an amount of about 0.01 to 1% by weight to said particles.

18. The method of claim 17 wherein said antifoaming agent comprises a high molecular weight alcohol, aldehyde, or a ketone having a vapor pressure of less than 2 mbar at 25° C.

19. The method of claim 9 further comprising passing a stream of gas through said bed of particles while maintaining said reduced pressure to evaporate said solvent.

* * * * *